(12) United States Patent
Cesura et al.

(10) Patent No.: US 6,667,327 B2
(45) Date of Patent: Dec. 23, 2003

(54) PYRIDINE AMIDO DERIVATIVES

(75) Inventors: Andrea Cesura, Crans-pres-Celigny (CH); Rosa Maria Rodriguez Sarmiento, Basel (CH); Andrew William Thomas, Birsfelden (CH); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/341,672

(22) Filed: Jan. 14, 2003

(65) Prior Publication Data

US 2003/0158235 A1 Aug. 21, 2003

(51) Int. Cl.$^7$ .................. A61K 31/44; C07D 213/63
(52) U.S. Cl. .................. 514/350; 546/298; 546/292; 546/291; 546/290; 514/346; 514/345
(58) Field of Search .................. 514/350, 346, 514/345; 546/298, 292, 291, 290

(56) References Cited

U.S. PATENT DOCUMENTS

| | | | |
|---|---|---|---|
| 4,764,522 A | | 8/1988 | Kyburz et al. |
| 4,776,876 A | * | 10/1988 | Nordhoff et al. ............ 71/92 |
| 5,446,066 A | | 8/1995 | Varasi et al. |

FOREIGN PATENT DOCUMENTS

| EP | 0 400 495 | 5/1990 |
|---|---|---|
| JP | 2-142774 | 5/1990 |
| WO | WO 99/14334 | 11/1990 |
| WO | WO 92/05163 | 4/1992 |
| WO | WO 97/05102 | 2/1997 |
| WO | WO 99/26614 | 6/1999 |
| WO | WO 99/35123 | 7/1999 |
| WO | WO 99/54279 | 10/1999 |
| WO | WO 00/75106 | 12/2000 |
| WO | WO 01/32649 | 5/2001 |
| WO | WO 01/56560 | 8/2001 |

OTHER PUBLICATIONS

Cesura, et al., *Eur. J. Pharmacol.* vol. 162, pp. 457–465 (1989).
C. J. Fowler, et al. *J. Neural. Transmission*, vol. 49, pp. 1–20 (1980).
M.S. Benedetti and I P. Dostert, *Biochem. Pharmacol.*, vol. 38, pp. 555–561 (1989).
Saura et al., *Neuroscience*, vol. 70, pp. 755–774 (1996).
D. Bentué–Ferrer et al., *CNS Drugs*, vol. 6, pp. 217–236 (1996).
A. Cesura & A. Pletscher, *Prog. Drug Research*, vol. 38, pp. 171–297 (1992).

* cited by examiner

Primary Examiner—Charanjit S. Aulakh
(74) Attorney, Agent, or Firm—George W. Johnston; Patricia S. Rocha-Tramaloni; Kimberly J. Prior

(57) ABSTRACT

Disclosed are pyridine amido derivatives of the formula

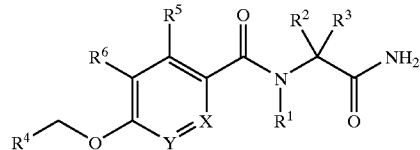

I wherein X, Y, and $R^1$ to $R^6$ are as defined herein. These compounds are selective MAO-B inhibitors and are useful in treating diseases such as, for example, Alzheimer's and senile dementia. Also disclosed are pharmaceutical compositions containing such compounds and a method of preparing such compounds.

16 Claims, No Drawings

PYRIDINE AMIDO DERIVATIVES

BRIEF SUMMARY OF THE INVENTION

This invention relates to novel pyridine amido derivatives that are selective monoamine oxidase B ("MAO-B") inhibitors. This invention also relates to pharmaceutical compositions containing these compounds and methods of treatment of diseases that are mediated by monoamine oxidase B inhibitors, such as, for example, Alzheimer's disease and senile dementia.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes (A. W. Bach et al., *Proc. Natl. Acad. Sci. USA* 1988, 85, 4934–4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, *Prog. Drug Research* 1992, 38, 171–297). Brain MAO-B activity appears to increase with age. This increase has been attributed to the gliosis associated with aging (C. J. Fowler et al., *J. Neural. Transm.* 1980, 49, 1–20). Additionally, MAO-B activity is significantly higher in the brains of patients with Alzheimer's disease (P. Dostert et al., *Biochem. Pharmacol.* 1989, 38, 555–561) and it has been found to be highly expressed in astrocytes around senile plaques (Saura et al., *Neuroscience* 1994, 70, 755–774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in *CNS Drugs* 1996, 6, 217–236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99–104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

DETAILED DESCRIPTION OF THE INVENTION

Definitions

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$C_1$–$C_6$-alkyl" ("lower alkyl") used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

The term "halogen" denotes fluorine, chlorine, bromine and iodine.

"Halogenalkyl" or "halogen-($C_1$–$C_6$)-alkyl" means the lower alkyl residue as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like.

"Alkoxy" or "($C_1$–$C_6$)-alkoxy" means the residue —O—R, wherein R is a lower alkyl residue as defined herein. Examples of alkoxy radicals include, but are not limited to, methoxy, ethoxy, isopropoxy, and the like.

"Aryl" represents an aromatic carbocyclic group consisting of one individual ring, or one or more fused rings in which at least one ring is aromatic in nature. Preferred aryl groups are phenyl or naphthyl. Especially preferred is phenyl.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, 2,2,2-trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

Similarly, a "pharmaceutically acceptable carrier" or "excipient" means a pharmacologically acceptable and substantially non-toxic, inert, carrier or excipient. Such carriers and excipients are further discussed infra.

Preferred Embodiments

In one embodiment, this invention relates to pyridine amido derivatives of the formula

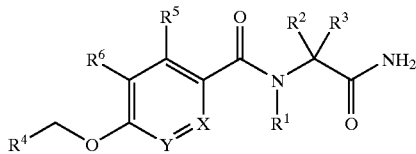

wherein
one of X or Y is —N= and the other one is —CR$^7$=;
$R^1$ is hydrogen or $C_1$–$C_6$-alkyl;
$R^2$ is hydrogen or $C_1$–$C_6$-alkyl;
$R^3$ is hydrogen or $C_1$–$C_6$-alkyl;
$R^4$ is selected from the group halogen-($C_1$–$C_6$)-alkyl, unsubstituted aryl, and aryl substituted by one or more substituents selected from the group $C_1$–$C_6$-alkyl, halogen, halogen-($C_1$–$C_6$)-alkyl, ($C_1$–$C_6$)-alkoxy and cyano;
$R^5$ is hydrogen or $C_1$–$C_6$-alkyl;
$R^6$ is hydrogen or $C_1$–$C_6$-alkyl; and
$R^7$ is hydrogen or $C_1$–$C_6$-alkyl;
or the pharmaceutically acceptable salts of said compounds.

The compounds of formula I of the present invention and their pharmaceutically acceptable salts are highly selective MAO-B inhibitors.

The present invention also relates to pharmaceutical compositions comprising a pharmaceutically effective amount of any one or more compound of formula I in accordance with the invention or a pharmaceutically acceptable salt thereof, and a pharmaceutically acceptable carrier or excipient, as well as to the use of the compounds of formula I in the control or prevention of diseases mediated by monoamine oxidase B inhibitors.

In another embodiment the invention relates to a process for the preparation of compounds of formula I and their pharmaceutically acceptable salts preparation.

Preferred compounds of formula I are those in which X is —N=. More preferred are those compounds of formula I wherein X is —N= and $R^4$ is unsubstituted aryl or aryl substituted by one or more substituents selected from the group consisting of $C_1$–$C_6$-alkyl, halogen, halogen-($C_1$–$C_6$)-alkyl, ($C_1$–$C_6$)-alkoxy and cyano. Most preferred are compounds of formula I wherein X is —N= and $R^4$ is phenyl or phenyl substituted by one or more substituents selected from the group consisting of $C_1$–$C_6$-alkyl, halogen, halogen-($C_1$–$C_6$)-alkyl, ($C_1$–$C_6$)-alkoxy and cyano.

Especially preferred are compounds of formula I in which X is —N= and $R^4$ is phenyl substituted by one or more halogen atoms. Examples of such compounds are the following:
5-(3-fluoro-benzyloxy)-pyridine-2-carboxylic acid carbamoylmethyl-amide,
5-(4-fluoro-benzyloxy)-pyridine-2-carboxylic acid carbamoylmethyl-amide,
5-(3,4-difluoro-benzyloxy)-pyridine-2-carboxylic acid carbamoylmethyl-amide,
(S)-5-(3-ifluoro-benzyloxy)-pyridine-2-carboxylic acid (1-carbamoyl-ethyl)-amide,
(S)-5- (4-fluoro-benzyloxy)-pyridine-2-carboxylic acid (1-carbamoyl-ethyl)-amide, and
(S)-5- (3,4-difluoro-benzyloxy)-pyridine-2-carboxylic acid (1-carbamoyl-ethyl)-amide.

Also preferred are compounds of formula I in which Y is —N=. More preferred are compounds of formula I in which Y is —N= and $R^4$ is unsubstituted aryl or aryl substituted by one or more substituents selected from the group consisting of $C_1$–$C_6$-alkyl, halogen, halogen-($C_1$–$C_6$)-alkyl, ($C_1$–$C_6$)-alkoxy and cyano. Most preferred are compounds of formula I wherein Y is —N= and $R^4$ is phenyl or phenyl substituted by one or more substituents selected from the group consisting of $C_1$–$C_6$-alkyl, halogen, halogen-($C_1$–$C_6$)-alkyl, ($C_1$–$C_6$)-alkoxy and cyano.

Particularly preferred compounds of formula I are those in which Y is —N= and $R^4$ is phenyl or phenyl substituted by one or more halogen atoms. Examples of such compounds are the following:
6-Benzyloxy-N-carbamoylmethyl-nicotinamide,
N-Carbamoylmethyl-6-(3-fluoro-benzyloxy)-nicotinamide,
N-Carbamoylmethyl-6-(4-fluoro-benzyloxy)-nicotinamide,
(S)-6-Benzyloxy-N-(1-carbamoyl-ethyl)-nicotinamide,
(S)-N-(1-Carbamoyl-ethyl)-6-(3-fluoro-benzyloxy)-nicotinamide, and
(S)-N-(1-Carbamoyl-ethyl)-6-(4-fluoro-benzyloxy)-nicotinamide.

The compounds of formula I and their pharmaceutically acceptable salts can be prepared by reacting a compound of formula

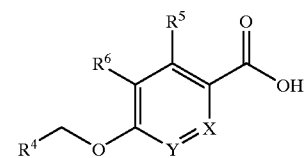

wherein X, Y, $R^4$, $R^5$ and $R^6$ are as defined herein above, with a compound of formula

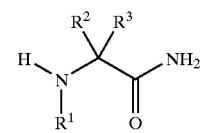

wherein $R^1$, $R^2$ and $R^3$ are as defined herein above, to obtain a compound of formula

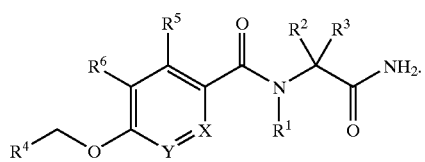

If desired, a compound of formula I can then be converted to a pharmaceutically acceptable salt by methods known to those skilled in the art.

In accordance with the present invention, compounds of formula I wherein X is —N= and Y is —CR$^7$= (hereinafter referred to as compounds of formula Ia), can be manufactured by coupling an appropriate pyridine-2-carboxylic acid derivative of formula IIa wherein $R^4$ is an optionally substituted aryl group or a halogenalkyl group such as 1,1,1-trifluoropropyl and $R^5$, $R^6$ and $R^7$ are hydrogen or alkyl with a 2-aminoacetamide of formula III wherein $R^1$, $R^2$ and $R^3$ are hydrogen or alkyl (Scheme 1 below).

Scheme 1

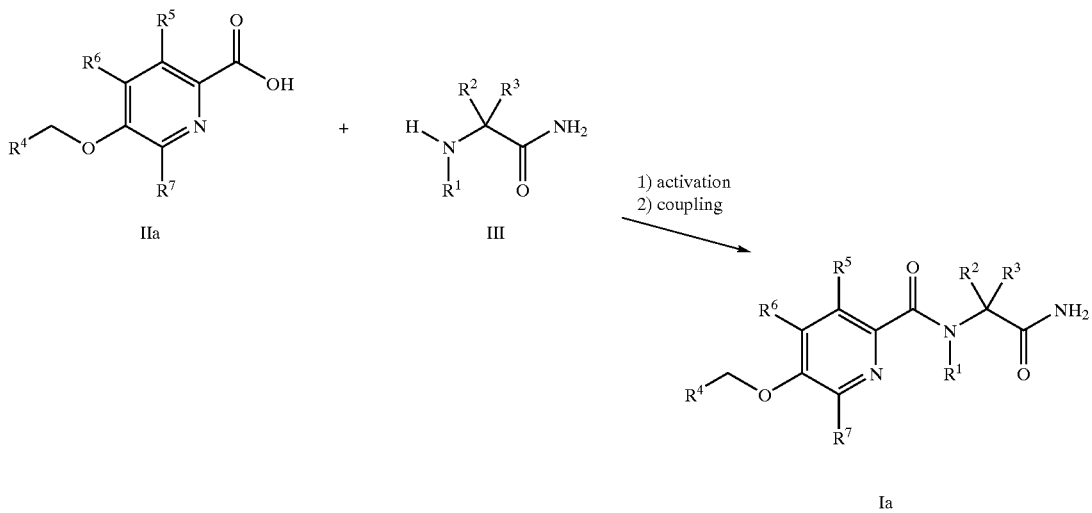

Coupling the carboxylic acid with an amine (or amino acid) can be accomplished using standard methods for the preparation of amides (or peptides), for example by treating the mixture of the acid and the amine with 1 equivalent of N-(3-dimethylamino-propyl)-N'-ethyl-carbodiimide hydrochloride (EDC) and 0.5 equivalents of 4-dimethyl-amino pyridine (DMAP). The amides can also be prepared by methods where the acid is first activated as the acid chloride or by treatment of with a suitable activating agent such as 1,1'-carbonyl-diimidazole (CDI).

The pyridine-2-carboxylic acid derivatives of formula IIa can be prepared from a 6-hydroxymethyl-pyridin-3-ol hydrochloride IV and a bromide of formula V in the presence of a base like potassium carbonate in a solvents like 2-butanone. After heating to 80° C. a pyridin-2-yl-methanol of formula VI is obtained which can be oxidized with manganese dioxide to the corresponding pyridine-2-carbaldehyde of formula VII. The carboxylic acid derivatives of formula IIha can be obtained from VII by oxidation with hydrogen peroxide and with a catalytic amount of manganese dioxide under reflux (Scheme 2 below).

Scheme 2

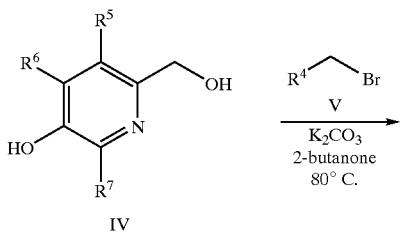

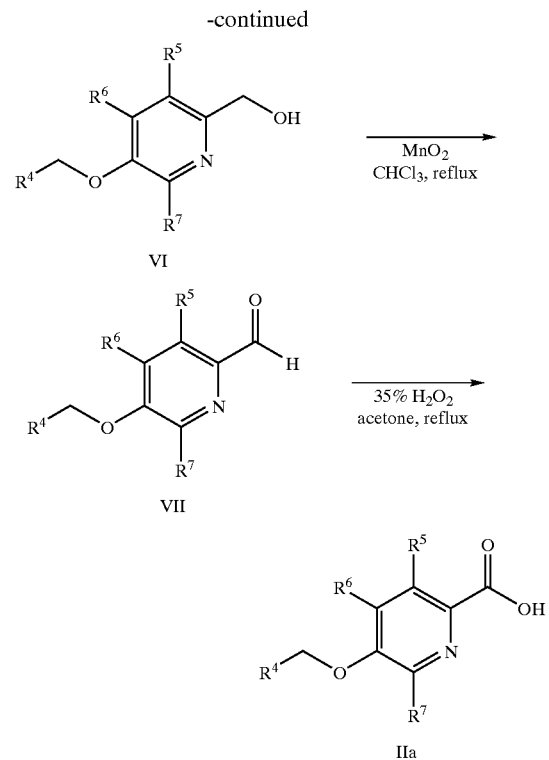

Compounds of formula I wherein X signifies —CR$^7$= and Y is —N= (hereinafter designated compounds of formula Ib), can be prepared accordingly by reacting a nicotinic acid derivative of formula IIb wherein R$^4$ is an optionally substituted aryl group or a halogenalkyl group such as 1,1,1-trifluoro-propyl and R$^5$, R$^6$ and R$^7$ are hydrogen or alkyl with a 2-aminoacetamide of formula III wherein R$^1$, R$^2$ and R$^3$ are hydrogen or alkyl (Scheme 3 below).

Scheme 3

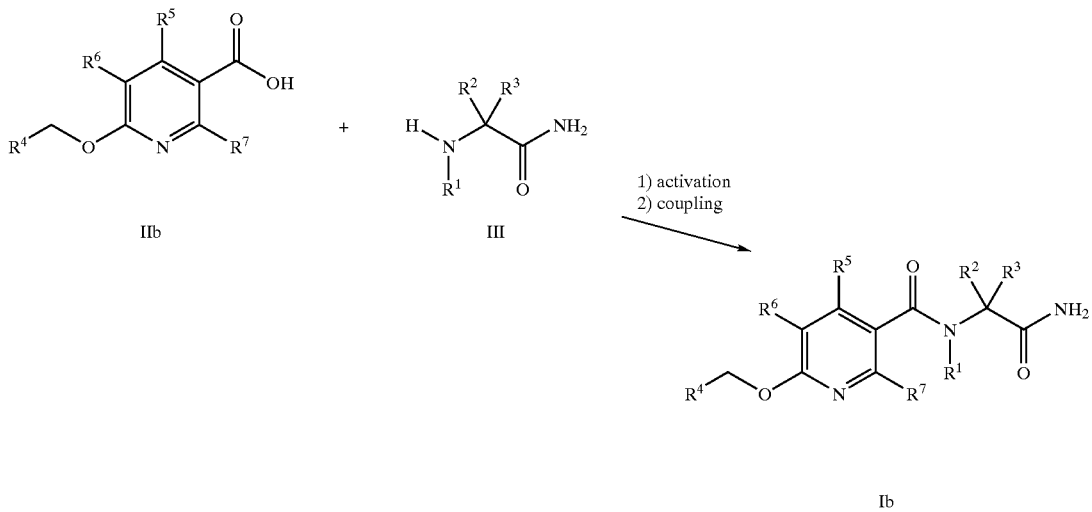

Compounds of formula IIb can be prepared by reacting 6-chloronicotinic acid IX with an alcohol of formula VIII wherein $R^4$ is an optionally substituted aryl group or a halogenalkyl group in the presence of a base such as potassium hydroxide and in a polar solvent such as dimethylsulfoxide (DMSO). The reaction is preferably carried out at elevated temperature (such as for example 140° C.) (Scheme 4 below).

Scheme 4

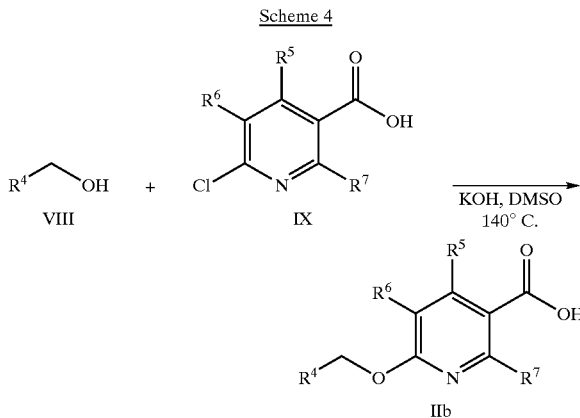

Pharmaceutically acceptable salts of compounds of formula I can be manufactured readily according to methods known to those skilled in the art, taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications include reward deficiency syndrome (G. M. Sullivan, International patent application No. WO 01/34172 A2), peripheral neuropathy caused by cancer chemotherapy (G. Bobotas, International Patent Application No. WO 97/33572 A1), the treatment of multiple sclerosis (R. Y. Harris, International patent application No. WO 96/40095 A1) and other neuroinflammatory diseases.

The pharmacological activity of the compounds of the invention was tested using the following method:

The cDNA's encoding human MAO-A and MAO-B were transiently transfected into EBNA cells using the procedure described by E.-J. Schlaeger and K. Christensen (Transient Gene Expression in Mammalian Cells Grown in Serum-free Suspension Culture; Cytotechnology, 15: 1–13, 1998). After transfection, cells were homogeneised by means of a Polytron homogeneiser in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B activities were assayed by [$^3$H]Ro 41-1049 [tritiated N-(2-aminoethyl)-5-(3-fluorophenyl)-4-thiazole-carboxamide] and [$^3$H] Ro 19-6327 [tritiated N-(2-aminoethyl)-5-chloro-2-pyridinecarboxamide, [$^3$H] lazabemide] binding, respectively, following the methods described by Cesura et al. (Characterization of the binding of [$^3$H]Ro 41-1049 to the active site of monoamine oxidase-A, Molec. Pharmacol. 1990, 37, 358–366; [$^3$H]Ro 19-6327:

a reversible ligand and affinity-labeling probe for monoamine oxidase-B, Eur. J. Pharmacol., 1989, 162, 457–465). Briefly, membrane aliquots were incubated in the presence of 20 nM [$^3$H]Ro 41-1049 (MAO-A assay) and [$^3$H]Ro 19-6327 (MAO-B assay) for 1 hour at 37° C. and 25° C., respectively, with or without various concentrations of the compounds, in a final volume of 0.2 ml. The incubation buffer consisted of 50 mM Tris, 130 mM NaCl, 5 mM KCl, 1 mM MgCl$_2$, 0.5 mM EGTA, buffered to pH 7.4 with HCl. The assay was terminated by filtering the samples through GF/C filters (Unifilter-96, Canberra Packard). The radioactivity retained on the filters was eventually counted for radioactivity by means of a Packard Top-Count scintillation counter, after addition of Microscint 40 scintillation fluid (Canberra Packard). Non-specific binding was determined in the presence of 10 µM clorgyline for MAO-A or 10 µM L-deprenyl for MAO-B.

IC$_{50}$ values, that is, the concentration of a test compound of formula I required to inhibit the MAO-B enzyme activity by 50%, were determined from inhibition curves obtained using nine inhibitor concentrations in duplicate, by fitting data to a four parameter logistic equation using a computer program.

The compounds of the present invention are specific MAO-B inhibitors. The activities of compounds of formula I as measured in the above-described assay are in the range of 10 µM or less, typically of 1 µM or less, preferable 0.3 µM or less, and ideally 0.1 µM or less. In the table below are described some specific IC$_{50}$ values of preferred compounds.

| Compound | IC$_{50}$ MAO-B (µM) | IC$_{50}$ MAO-A (µM) |
|---|---|---|
| 6-benzyloxy-N-carbamoylmethyl-nicotinamide (Example 1) | 0.033 | >10 |
| N-carbamoylmethyl-6-(3-fluoro-benzyloxy)-nicotinamide (Example 2) | 0.030 | 4.150 |
| 5-(3-fluoro-benzyloxy)-pyridine-2-carboxylic acid carbamoylmethyl-amide (Example 7) | 0.028 | 9.160 |
| 5-(4-fluoro-benzyloxy)-pyridine-2-carboxylic acid carbamoylmethyl-amide (Example 8) | 0.030 | >10 |
| 5-(3,4-difluoro-benzyloxy)-pyridine-2-carboxylic acid carbamoylmethyl-amide (Example 9) | 0.043 | >10 |
| (S)-5-(4-fluoro-benzyloxy)-pyridine-2-carboxylic acid(1-carbamoyl-ethyl)-amide (Example 11) | 0.070 | >10 |

The compounds of formula I and pharmaceutically acceptable salts thereof can be used to prepare pharmaceutical compositions. The pharmaceutical compositions containing compounds of formula I preferably are administered orally, e.g. in the form of tablets, coated tablets, dragees, hard and soft gelatin capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary.

Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

As mentioned earlier, the invention also relates to pharmaceutical preparations containing a compound of formula I, or pharmaceutically acceptable salts thereof, and one or more therapeutically inert carrier and/or excipient.

The therapeutically effective amount of a compound of formula 1, or a pharmaceutically acceptable salt thereof, that is the dosage, can vary within wide limits and will, of course, be fitted to the individual requirements in each particular case. In general, the effective dosage for oral or parenteral administration is between 0.01–20 mg/kg/day, with a dosage of 0.1–10 mg/ kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof.

EXAMPLE 1

6-Benzyloxv-N-carbamoylmethyl-nicotinamide a) 6-Benzyloxa-nicotinic Acid

A mixture of 6-chloronicotinic acid (3 g, 19 mmol), benzyl alcohol (4.1 g, 38 mmol), KOH (4.27 g, 76 mmol) and DMSO (30 ml) was heated at 140° C. for 15 min. After cooling, water was added and the solution acidified to pH 4 with 1 N HCl. The precipitate was filtered and washed with water. The solid was then dissolved in methylene chloride and dried with Na$_2$SO$_4$. Filtration and evaporation of the solvent left a solid which was triturated with ether to give the title acid as a white crystalline solid (3.29 g, 75%). MS: m/e=228.1 (M–H$^+$).

b) 6-Benzyloxy-N-carbamoylmethyl-nicotinamide

A mixture of 6-benzyloxy-nicotinic acid (500 mg, 2.18 mmol), glycinamide HCl (265 mg, 2.4 mmol), 4-dimethylamino pyridine (133 mg; 1.09 mmol), N-(3-dimethylamino-propyl)-N'-ethylcarbodiimide HCl (460 mg; 2.4 mmol) and methylene chloride (10 ml) was stirred at 0° C. for 1 h then at r.t. overnight. The precipitate was filtered off and washed with methylene chloride and water. The title compound was obtained as a white solid (328 mg; 53%). MS: m/e=286.2 (M+H$^+$).

EXAMPLE 2

N-Carbamoylmethyl-6-(3-fluoro-benzyloxy)-nicotinamide a) 6-(3-Fluoro-benzyloxv)-nicotinic Acid As described in example 1a, 6-(3-fluoro-benzyloxy)-nicotinic acid was prepared from 6-chloronicotinic acid and 3-fluoro benzyl alcohol to give a tan solid. MS: m/e=246.2 (M–H$^+$).

b) N-Carbamoylmethyl-6-(3-fluoro-benzyloxy)-nicotinamide

As described in Example 1b, 6-(3-fluoro-benzyloxy)-nicotinic acid was converted to the title compound which was obtained as a white solid. MS: m/e=304.3 (M+H$^+$).

EXAMPLE 3

N-Carbamoylmethyl-6-(4-fluoro-benzyloxv)-nicotinamide a) 6-(4-Fluoro-benzyloxy)-nicotinic Acid As described in Example 1a, 6-(4-fluoro-benzyloxy)-nicotinic acid was prepared from 6-chloronicotinic acid and 4-fluoro benzyl alcohol to give a tan solid. MS: m/e=246.2 (M−H$^+$).

b) N-Carbamoylmethyl-6-(4-fluoro-benzyloxy)-nicotinamide

As described in Example 1b, 6-(4-fluoro-benzyloxy)-nicotinic acid was converted to the title compound which was obtained as a white solid. MS: m/e=304.3 (M+H$^+$).

EXAMPLE 4

(S)-6-Benzyloxv-N-(1-carbamoyl-ethyl)-nicotinamide

As described for Example 1b, 6-benzyloxy-nicotinic acid which was prepared as described in Example Ia, was converted to the title compound (using H-alanine-NH$_2$ HCl instead of glycinamide HCl) which was obtained as a white solid. MS: m/e=300.3 (M+H$^+$).

EXAMPLE 5

(S)-N-(1-Carbamoyl-ethyl)-6-(3-fluoro-benzyloxy)-nicotinamide

In analogy to the procedure described in Example 1b, 6-(3-fluoro-benzyloxy)-nicotinic acid (see Example 2a) was converted to the title compound (using H-Alanine-NH$_2$ HCl instead of glycinamide HCl) which was obtained as a white solid. MS: m/e=318.3 (M+H$^+$).

EXAMPLE 6

(S)-N-(1-Carbamoyl-ethyl)-6-(4-fluoro-benzyloxy)-nicotinamide

As described for Example 1b, 6-(4-fluoro-benzyloxy)-nicotinic acid (see Example 3a) was converted to the title compound (using H-Alanine-NH$_2$ HCl instead of glycinamide HCl) which was obtained as a white solid. MS: mle=340.3 (M+Na$^+$).

EXAMPLE 7

5-(3-Fluoro-benzyloxy)-pyridine-2-carboxylic Acid Carbamoylmethyl-amide a) [5-(3-Fluoro-benzyloxy)-pyridin-2-yl]-methanol A mixture of 6-hydroxymethyl-pyridin-3-ol hydrochloride (1:1) (6.29 g, 38.9 mmol), 3-fluorobenzyl bromide (8.1 g, 42.8 mmol), potassium carbonate (10.76 g, 77.9 mmol) and 2-butanone (200 ml) was heated to 80° C. for 5 h. After cooling, water was added, and the mixture extracted with ethyl acetate. After drying of the organic layer with MgSO$_4$, filtration and evaporation, the residue was purified by chromatography (SiO$_2$, CH$_2$Cl$_2$—MeOH 95:5) to give the title compound as a brown solid (6.12 g, 67%). MS: m/e=234.3 (M+H$^+$).

b) 5-(3-Fluoro-benzyloxy)-pyridine-2-carbaldehyde

A mixture of [5-(3-fluoro-benzyloxy)-pyridin-2-yl]-methanol (3.8 g, 16.3 mmol), MnO$_2$ (12 g, 138 mmol) and chloroform (50 ml) was heated under reflux for 30 min. The dark solids were then removed by filtration over celite. The filtrate was evaporated and the residue purified by chromatography (SiO$_2$, AcOEt-hexanes 1:1) to afford the title compound (3.0 g, 80%) as a light yellow oil with solidified on standing. MS: m/e=232.2 (M+H$^+$).

c) 5-(3-Fluoro-benzyloxy)-pyridine-2-carboxylic Acid

A mixture of 5-(3-fluoro-benzyloxy)-pyridine-2-carbaldehyde (600 mg, 2.6 mmol), hydrogen peroxide (aq. 35%, 4 ml, 118 mmol) acetone (20 ml) and a catalytic amount of MnO$_2$ was heated under reflux for 4 h. The solvent was evaporated and the residue was triturated with water. The precipitate was collected to give the title compound as a white solid (628 mg, 98%). MS: m/e =247.1 (M$^+$).

d) 5-(3-Fluoro-benzyloxy)-pyridine-2-carboxylic Acid Carbamoylmethyl-amide

As described for Example 1b, 5-(3-fluoro-benzyloxy)-pyridine-2-carboxylic acid was converted to the title compound which was obtained as a white solid. MS: m/e=304.3 (M+H$^+$).

EXAMPLE 8

5-(4-Fluoro-benzyloxy)-pyridine-2-carboxylic Acid Carbamoylmethyl-amide a) [5-(4-Fluoro-benzyloxy)-pyridin-2-yll-methanol As described in Example 7a, the title compound was obtained from 6-hydroxymethyl-pyridin-3-ol hydrochloride (1:1) and 4-fluorobenzyl bromide as a light brown solid. MS: m/e=233.2 (M+H$^+$).

b) 5-(4-Fluoro-benzyloxy)-pyridine-2-carbaldehyde

Following the procedure as described in Example 7b, [5-(4-fluoro-benzyloxy)-pyridin-2-yl]-methanol was converted to the title compound which was obtained as a light yellow solid. MS: m/e=232.2 (M+H$^+$).

c) 5-(4-Fluoro-benzyloxy)-pyridine-2-carboxylic Acid

As described in Example 7c, the title compound was obtained from 5-(4-fluoro-benzyloxy)-pyridine-2-carbaldehyde as a white solid. MS: m/e=246.2 (M−H$^+$).

d) 5-(4-Fluoro-benzyloxy)-pyridine-2-carboxylic acid carbamoylmethyl-amide

Following the general procedure described in Example 1b, 5-(4-Fluoro-benzyloxy)-pyridine-2-carboxylic acid was converted to the title compound which was obtained as a white solid. MS: m/e=304.2 (M+H$^+$).

EXAMPLE 9

5-(3.4-Difluoro-benzyloxy)-pyridine-2-carboxylic Acid Carbamoylmethyl-amide a) [5-(3,4-Difluoro-benzyloxy)-pyridin-2-yl]-methanol As described in Example 7a, the title compound was obtained from 6-hydroxymethyl-pyridin-3-ol hydrochloride (1:1) and 3,4-difluorobenzyl bromide as a light brown solid. MS: m/e=252.2 (M−H$^+$).

b) 5-(3,4-Difluoro-benzyloxy)-pyridine-2-carbaldehyde

As described in Example 7b, [5-(3,4-difluoro-benzyloxy)-pyridin-2-yl]-methanol was converted to the title compound which was obtained as a light brown solid. MS: m/e=250.2 (M+H$^+$).

c) 5-(3,4-Difluoro-benzyloxy)-pyridine-2-carboxylic Acid

As described in Example 7c, the title compound was obtained from 5-(3,4-difluoro-benzyloxy)-pyridine-2-carbaldehyde as a white solid. MS: m/e=264.0 (M−H$^+$).

d) 5-(3,4-Difluoro-benzyloxy)-pyridine-2-carboxylic Acid Carbamoylmethyl-amide

Following the general procedure described in Example 1d, 5-(3,4-difluoro-benzyloxy)-pyridine-2-carboxylic acid was converted to the title compound which was obtained as a light yellow solid. MS: m/e=322.4 (M+H⁺).

EXAMPLE 10

(S)-5-(3-Fluoro-benzyloxy)-pyridine-2-carboxylic Acid (1-carbamoyl-ethyl)-amide

Following the general procedure described in Example 1b, 5-(3-fluoro-benzyloxy)-pyridine-2-carboxylic acid (see Example 7c) was converted to the title compound (using H-alanine-NH₂ HCl instead of glycinamide HCl) which was obtained as a white solid. MS: m/e=318.3 (M+H⁺).

EXAMPLE 11

(S)-5-(4-Fluoro-benzyloxy)-pyridine-2-carboxylic Acid (1-carbamoyl-ethyl)-amide

Following the general procedure described in Example 1b, 5-(4-fluoro-benzyloxy)-pyridine-2-carboxylic acid (see Example 8c) was converted to the title compound (using H-alanine-NH₂ HCl instead of glycinamide HCl) which was obtained as a light brown solid. MS: m/e=336.3 (M+H⁺).

EXAMPLE 12

(S)-5-(3,4-Difluoro-benzyloxy)-pyridine-2-carboxylic Acid (1-carbamoyl-ethyl)-amide Following the general procedure described in Example 1b, 5-(3,4-difluoro-benzyloxy)-pyridine-2-carboxylic acid (see Example 9c) was converted to the title compound (using H-alanine-NH₂ HCl instead of glycinamide HCl) which was obtained as a light yellow solid. MS: m/e=336.3 (M+H⁺).

EXAMPLE A

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

EXAMPLE D

An injection solution may have the following composition and is manufactured in usual manner:

| Active substance | 1.0 mg |
| --- | --- |
| 1 N HCl | 20.0 µl |
| acetic acid | 0.5 mg |
| NaCl | 8.0 mg |
| phenol | 10.0 mg |
| 1 N NaOH | q.s. ad pH 5 |
| H₂O | q.s. ad 1 ml |

What is claimed is:

1. A compound of formula

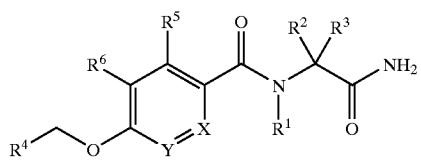

I wherein
one of X or Y is —N= and the other one is —CR⁷=;
R¹ is hydrogen or $C_1$–$C_6$-alkyl;
R² is hydrogen or $C_1$–$C_6$-alkyl;
R³ is hydrogen or $C_1$–$C_6$-alkyl;
R⁴ is selected from the group halogen-($C_1$–$C_6$)-alkyl, unsubstituted aryl, and aryl substituted by one or more substituents selected from the group $C_1$–$C_6$-alkyl, halogen, halogen-($C_1$–$C_6$)-alkyl, ($C_1$–$C_6$)-alkoxy and cyano;

R⁵ is hydrogen or $C_1$–$C_6$-alkyl;

R⁶ is hydrogen or $C_1$–$C_6$-alkyl; and

R⁷ is hydrogen or $C_1$–$C_6$-alkyl;

or a pharmaceutically acceptable salt thereof.

2. The compound of claim 1 wherein X is —N═.

3. The compound of claim 2 wherein R⁴ is unsubstituted aryl or aryl substituted by one or more substituents selected from the group $C_1$–$C_6$-alkyl, halogen, halogen-($C_1$–$C_6$)-alkyl, ($C_1$–$C_6$)-alkoxy and cyano.

4. The compound of claim 3 wherein R⁴ is phenyl or phenyl substituted by one or more substituents selected from the group $C_1$–$C_6$-alkyl, halogen, halogen-($C_1$–$C_6$)-alkyl, ($C_1$–$C_6$)-alkoxy and cyano.

5. The compound of claim 4 wherein R⁴ is phenyl substituted by one or more halogen atoms.

6. The compound of claim 5 which is selected from the group:

5-(3-fluoro-benzyloxy)-pyridine-2-carboxylic acid carbamoylmethyl-amide, 5-(4-fluoro-benzyloxy)-pyridine-2-carboxylic acid carbamoylmethyl-amide, 5-(3,4-difluoro-benzyloxy)-pyridine-2-carboxylic acid carbamoylmethyl-amide, (S)-5-(3-fluoro-benzyloxy)-pyridine-2-carboxylic acid (1-carbamoyl-ethyl)-amide, (S)-5-(4-fluoro-benzyloxy)-pyridine-2-carboxylic acid (1-carbamoyl-ethyl)-amide, and (S)-5-(3,4-difluoro-benzyloxy)-pyridine-2-carboxylic acid (1-carbamoyl-ethyl)-amide.

7. The compound of claim 1 wherein Y is —N═.

8. The compound of claim 7 wherein R⁴ is unsubstituted aryl or aryl substituted by one or more substituents selected from the group $C_1$–$C_6$-alkyl, halogen, halogen-($C_1$–$C_6$)-alkyl, ($C_1$–$C_6$)-alkoxy and cyano.

9. The compound of claim 8 wherein R⁴ is phenyl or phenyl substituted by one or more substituents selected from the group $C_1$–$C_6$-alkyl, halogen, halogen-($C_1$–$C_6$)-alkyl, ($C_1$–$C_6$)-alkoxy and cyano.

10. The compound of claim 9 wherein R⁴ is phenyl or phenyl substituted by one or more halogen atoms.

11. The compound of claim 10 which is selected from the group:

6-Benzyloxy-N-carbamoylmethyl-nicotinamide,

N-Carbamoylmethyl-6-(3-fluoro-benzyloxy)-nicotinamide,

N-Carbamoylmethyl-6-(4-fluoro-benzyloxy)-nicotinamide, (S)-6-Benzyloxy-N-(1-carbamoyl-ethyl)-nicotinamide, (S)-N-(1-Carbamoyl-ethyl)-6-(3-fluoro-benzyloxy)-nicotinamide, and (S)-N-(1-Carbamoyl-ethyl)-6-(4-fluoro-benzyloxy)-nicotinamide.

12. A process for the preparation of a compound of formula I comprising: reacting a compound of formula

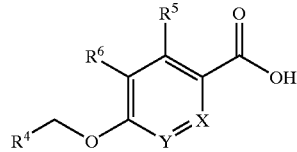

with a compound of formula

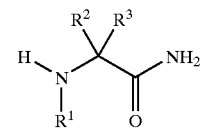

to obtain a compound of formula

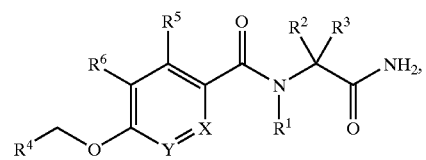

wherein one of X or Y is —N═ and the other one is —CR⁷═;

R¹ is hydrogen or $C_1$–$C_6$-alkyl;

R² is hydrogen or $C_1$–$C_6$-alkyl;

R³ is hydrogen or $C_1$–$C_6$-alkyl;

R⁴ is selected from the group halogen-($C_1$–$C_6$)-alkyl, unsubstituted aryl, and aryl substituted by one or more substituents selected from the group $C_1$–$C_6$-alkyl, halogen, halogen-($C_1$–$C_6$)-alkyl, ($C_1$–$C_6$)-alkoxy and cyano;

R⁵ is hydrogen or $C_1$–$C_6$-alkyl;

R⁶ is hydrogen or $C_1$–$C_6$-alkyl; and

R⁷ is hydrogen or $C_1$–$C_6$-alkyl.

13. A pharmaceutical composition comprising one or more compounds of claim 1 and a pharmaceutically acceptable excipient.

14. A method of treating Alzheimer's disease, comprising administering to a patient a therapeutically effective amount of a compound of claim 1.

15. A method of treating senile dementia, comprising administering to a patient a therapeutically effective amount of a compound of claim 1.

16. A method of treating Parkinson's disease, comprising administering to a patient a therapeutically effective amount of a compound of claim 1.

* * * * *

UNITED STATES PATENT AND TRADEMARK OFFICE
CERTIFICATE OF CORRECTION

PATENT NO.      : 6,667,327 B2
DATED           : December 23, 2003
INVENTOR(S)     : Andrea Cesura et al.

It is certified that error appears in the above-identified patent and that said Letters Patent is hereby corrected as shown below:

<u>Title page,</u>
Insert item:
-- [30]          Foreign Application Priority Data
         Feb 4, 2002 (EP)………………..02001969.1 --.

Signed and Sealed this

Eleventh Day of May, 2004

JON W. DUDAS
*Acting Director of the United States Patent and Trademark Office*